US012577601B2

(12) United States Patent　　　　　(10) Patent No.:　US 12,577,601 B2
Yabuki et al.　　　　　　　　　　　　(45) Date of Patent:　　Mar. 17, 2026

(54) PROTEIN PRODUCTION METHOD AND CELL-FREE PROTEIN SYNTHESIS KIT

(71) Applicants: TAIYO NIPPON SANSO CORPORATION, Tokyo (JP); RIKEN, Saitama (JP)

(72) Inventors: Takashi Yabuki, Tokyo (JP); Takanori Kigawa, Saitama (JP); Kae Higuchi, Saitama (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 1100 days.

(21) Appl. No.: 17/627,233

(22) PCT Filed: Jul. 16, 2020

(86) PCT No.: PCT/JP2020/027679
§ 371 (c)(1),
(2) Date: Jan. 14, 2022

(87) PCT Pub. No.: WO2021/015095
PCT Pub. Date: Jan. 28, 2021

(65) Prior Publication Data
US 2022/0251620 A1　　Aug. 11, 2022

(30) Foreign Application Priority Data
Jul. 19, 2019　(JP) ................................ 2019-134081

(51) Int. Cl.
*C12P 21/02*　　(2006.01)
*C12N 1/20*　　(2006.01)
*C12N 15/11*　　(2006.01)

(52) U.S. Cl.
CPC ................ *C12P 21/02* (2013.01); *C12N 1/20* (2013.01); *C12N 15/11* (2013.01); *C12N 2500/32* (2013.01); *C12N 2501/998* (2013.01); *C12N 2800/10* (2013.01)

(58) Field of Classification Search
CPC ........... C12P 21/02; C12N 1/20; C12N 15/11; C12N 2500/32; C12N 2501/998; C12N 2800/10; C12R 2001/01; C12R 2001/125; C12R 2001/19; C07K 14/195; C07K 14/245; C07K 14/32
See application file for complete search history.

(56) References Cited

U.S. PATENT DOCUMENTS

2007/0207520 A1　9/2007　Morishita et al.
2011/0262946 A1　10/2011　Roy et al.
2013/0316397 A1　11/2013　Airen et al.

FOREIGN PATENT DOCUMENTS

| EP | 1 655 375 | 5/2006 |
|---|---|---|
| JP | 4-200390 | 7/1992 |
| JP | 7-110236 | 11/1995 |
| JP | 2005-6646 | 1/2005 |
| JP | 2007-259852 | 10/2007 |

OTHER PUBLICATIONS

Fujii et al. (Cloning of two cold shock genes, cspA and cspG from deep-sea psychrophilic bacterium Shewanella violacea strain DSS12., FEMS Microbiology Letters 178 (1999): 123-128) (Year: 1999).*
Extended European Search Report mailed Aug. 28, 2023 in European Application No. 20843121.3, 9 pages.
Hofweber Roland et al: "The influence of cold shock proteins on transcription and translation studied in cell-free model systems", The Febs Journal, vol. 272, No. 18, Sep. 1, 2005 (Sep. 1, 2005), pp. 4691-4702, XP093074335, GB, ISSN: 1742-464X, DOI: 10.1111/j.1742-4658.2005.04885.x.
Freischmidt Axel et al: "Enhanced in vitro translation at reduced temperatures using a cold-shock RNA motif", Biotechnology Letters, vol. 35, No. 3, Nov. 10, 2012 (Nov. 10, 2012), pp. 389-395, XP093074363, Dordrecht, ISSN: 0141-5492, DOI: 10.1007/s10529-012-1091-4.
Nakashima N et al: "Cell-free protein synthesis using cell extract of Pseudomonas fluorescens and CspA promoter", Biochemical and Biophysical Research Communications, Elsevier, Amsterdam NL, vol. 319, No. 2, Jun. 25, 2004 (Jun. 25, 2004), pp. 671-676, XP004512488, ISSN: 0006-291X, DOI: 10.1016/J.BBRC.2004.05.034.
International Search Report with English Translation for PCT/JP2020/027679 mailed Sep. 24, 2020, 5 pages.
Mujacic et al., "Cold-inducible cloning vectors for low-temperature protein expression in *Escherichia coli*: application to the production of a toxic and proteolytically sensitive fusion protein", Gene—An International Journal on Genes and Genomes, Dec. 16, 1998, pp. 325-332.
Qing et al., "Cold-shock induced high-yield protein production in *Escherichia coli*", Nature Biotechnology, vol. 22, No. 7, Jul. 2004, pp. 877-882.
Higuchi et al., "Cold shock proteins improve *E. coli* cell-free synthesis in terms of soluble yields of aggregation-prone proteins", Biotechnology Bioengineering, vol. 117, Mar. 12, 2020, pp. 1628-1639.
Higuchi et al., "Construction of Cell-Free Synthesis System Suitable for Low-Temperature Protein Expression", Proceedings of the 42nd Annual Meeting of the Molecular Biology Society of Japan, Nov. 19, 2019, 4 pages.

* cited by examiner

*Primary Examiner* — Iqbal H Chowdhury
(74) *Attorney, Agent, or Firm* — Nixon & Vanderhye P.C.

(57)　　　　　ABSTRACT

The object of the present invention is to provide a protein production method capable of producing an active protein with high efficiency even at a low temperature, and a cell-free protein synthesis kit. A protein production method including producing a protein with a reaction solution of a cell-free protein synthesis system containing either one or both of a cold shock protein and a nucleic acid containing a coding region encoding an amino acid sequence of the cold shock protein. A cell-free protein synthesis kit including one or both of a cold shock protein and a nucleic acid containing a coding region encoding an amino acid sequence of the cold shock protein, and a reaction solution of a cell-free protein synthesis system.

9 Claims, 14 Drawing Sheets

15% Tricine-PAGE CBB staining

T:Total fraction
S:Soluble fraction

PROTEIN PRODUCTION METHOD AND CELL-FREE PROTEIN SYNTHESIS KIT

This application is the U.S. national phase of International Application No. PCT/JP2020/027679 filed Jul. 16, 2020 which designated the U.S. and claims priority to JP 2019-134081 filed Jul. 19, 2019, the entire contents of each of which are hereby incorporated by reference.

TECHNICAL FIELD

The present invention relates to a protein production method and a cell-free protein synthesis kit.

Priority is claimed on Japanese Patent Application No. 2019-134081, filed Jul. 19, 2019, the contents of which are incorporated herein by reference.

BACKGROUND ART

As a method for producing a protein, a method using a cell-free protein synthesis system is known. The cell-free protein synthesis system is a technique to synthesize a protein in vitro by adding amino acids as substrates, an energy source such as adenosine triphosphate (ATP), an energy regeneration system, and a salt such as magnesium ions, as well as a gene encoding a target protein, to a cell extract containing factors necessary for protein synthesis. As the cell extract, those derived from *Escherichia coli*, insect cells, wheat germs, tobacco cells and animal cells are known, and kits thereof are commercially available.

Cell-free protein synthesis systems are used not only in basic research but also in application fields such as molecular diagnostics and high-throughput screening for pharmaceutical targets. A technology for dramatically increasing the yield of protein synthesis has been developed (Patent Documents 1 and 2), and such a technology is now being used for a large amount of synthesis of protein samples for three-dimensional structure analysis by X-ray crystallography, NMR, etc.

The cell-free protein synthesis system has the following advantages over the cell expression system using living organisms.

(1) Free choice of reaction conditions.

(2) Linear DNA such as a PCR product being usable as an expression construct, as well as circular DNA obtained by cloning the target gene.

(3) Easy synthesis of various labeled proteins.

(4) Easy synthesis of a protein having cytotoxicity.

(5) Automation being possible.

In a cell-free protein synthesis system using a cell extract derived from *Escherichia coli*, the yield of protein synthesis increases with the reaction temperature being set at 30 to 37° C. However, depending on the protein, the synthesis at 30 to 37° C. may result in precipitation without proper formation of a higher-order structure of the protein, or production of inactive proteins.

With regard to a protein expression system using *Escherichia coli* as a host, it is known that the expression level of an active protein increases by lowering the culture temperature for *Escherichia coli* (Non-Patent Documents 1 and 2). This is presumably because the translation speed is reduced and hence a sufficient time is allowed for proper folding of the target protein, and the low temperature environment reduces the activity of proteases, which in turn increases the stability of the produced protein.

Even in a cell-free protein synthesis system, precipitation may be suppressed by lowering the reaction temperature to approximately 20° C., but a low reaction temperature tends to significantly decrease the yield of the protein synthesis. It is also economically important to efficiently obtain a soluble and active protein with the smallest possible amount of reaction solution.

DESCRIPTION OF PRIOR ART

Patent Document

Patent Document 1: Japanese Examined Patent Application Publication No. Hei 7-110236

Patent Document 2: Japanese Unexamined Patent Application, First Publication No. Hei 4-200390

Non-Patent Document

Non-Patent Document 1: Mujacic, M., Cooper, K. W. and Baneyx, F. (1999) Gene 238, 325-332.

Non-Patent Document 2: Qing, G., Ma, L. C., Khorchid, A., Swapna, G. V., Mal, T. K., Takayama, M. M., Xia, B., Phadtare, S., Ke, H., Acton, T., Montelione, G. T., Ikura, M. and Inouye, M. (2004) Nat. Biotechnol. 22, 877-882.

DISCLOSURE OF INVENTION

Problems to be Solved by the Invention

The object of the present invention is to provide a protein production method capable of producing an active protein with high efficiency even at a low temperature, and a cell-free protein synthesis kit.

Means to Solve the Problems

In view of the above problems, the present inventors have investigated the effects of various cold shock proteins concerning adaptation to a low temperature environment on the synthetic activity in a cell-free protein synthesis system, and the solubility of the synthesized protein. As a result, it has been found that the use of a cold shock protein enables the protein synthesis to be implemented by a cell-free protein synthesis system with high protein synthesis activity even at a low temperature of lower than 30° C. The present invention has been completed based on this finding.

The present invention has the following configurations.

[1] A protein production method including producing a protein with a reaction solution of a cell-free protein synthesis system containing either one or both of a cold shock protein and a nucleic acid containing a coding region encoding an amino acid sequence of the cold shock protein.

[2] The protein production method according to [1], wherein the cold shock protein is CspA, CspB, CspC, CspE, CspG, or CspI derived from *Escherichia coli*.

[3] The protein production method according to [2], wherein the cold shock protein is CspA derived from *Escherichia coli*.

[4] The protein production method according to [1], wherein the cold shock protein is SliCspC derived from *Shewanella livingstonensis* of the genus *Shewanella*.

[5] The protein production method according to [1], wherein the cold shock protein is BsuCspB derived from *Bacillus subtilis* of the genus *Bacillus*.

[6] The protein production method according to any one of [1] to [5], which is implemented at a reaction temperature of 4 to 30° C.

[7] The protein production method to any one of [1] to [6], wherein the reaction solution contains the cold shock protein in an amount of 0.5 to 1.5 µg/µL.

[8] The protein production method according to any one of [1] to [7], wherein the reaction solution is a solution containing a cell extract.

[9] The protein production method according to [8], wherein the cell extract is a cell extract derived from *Escherichia coli*.

[10] The protein production method according to [9], wherein the reaction solution contains an L-amino acid, a buffer solution, a salt, an energy source, and an energy regeneration system.

[11] A cell-free protein synthesis kit including one or both of a cold shock protein and a nucleic acid containing a coding region encoding an amino acid sequence of the cold shock protein, and a reaction solution of a cell-free protein synthesis system.

Effect of the Invention

The present invention can provide a protein production method capable of producing an active protein with high efficiency even at a low temperature, and a cell-free protein synthesis kit.

DESCRIPTION OF THE EMBODIMENTS

Figure 1:
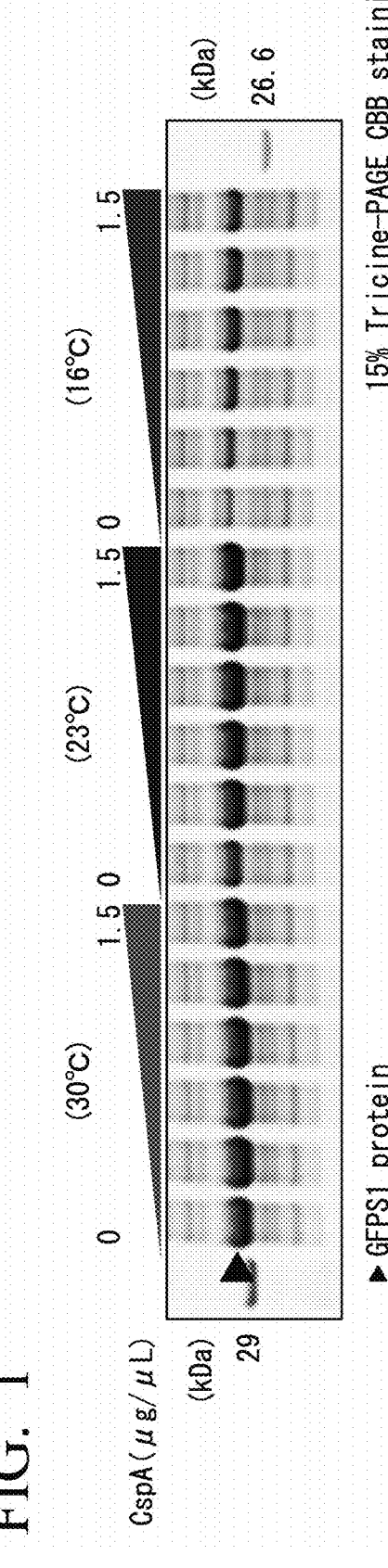
FIG. 1 shows the electrophoresis results with respect to the product of GFPS1 synthesis performed in Example 1.

In the specification and claims, the following terms should be understood as defined below.

The "cell-free protein synthesis system" is a system for synthesizing a target protein by taking out protein factors necessary for protein translation as a cell extract and reconstructing the intracellular reaction system in vitro. The cell-free protein synthesis system encompasses both of: cell-free transcription-translation systems including a cell-free transcription system that synthesizes RNA using DNA as a template, and a cell-free translation system that reads mRNA information and synthesizes a protein on a ribosome; and cell-free translation systems.

The "cold shock protein" means a protein or a protein domain having an amino acid sequence that matches the CSD family (PF00313) of the Pfam database (version 32.0) with a score of 100 or higher.

In the context of the present specification, "to" indicating a numerical range means that the numerical values described before and after "to" are included as the lower limit and the upper limit of the range.

[Protein Production Method]

The protein production method of the present invention is a method including producing a target protein with a reaction solution of a cell-free protein synthesis system containing either one or both of a cold shock protein (hereinafter also referred to as "Csp") and a nucleic acid containing a coding region encoding an amino acid sequence of the Csp (hereinafter also referred to as "Csp template nucleic acid"). The target protein can be produced by adding a template nucleic acid (DNA or mRNA) containing a coding region encoding the amino acid sequence of the target protein to a reaction solution.

The cell-free protein synthesis system may use a cell extract extracted from cells containing components necessary for the cell-free protein synthesis system, or a solution used in the reconstituted cell-free protein synthesis method, into which separately purified factors required for protein synthesis have been mixed. Examples of the factors required for protein synthesis include ribosomes, aminoacyl-tRNA synthases, tRNAs, translation terminators and the like.

As the reaction solution, a solution containing a cell extract is preferable.

Examples of the cell extract include cell extracts extracted from plant cells, animal cells, fungal cells, and bacterial cells, each containing components required for translation systems involved in protein synthesis, such as ribosomes, aminoacyl-tRNA synthases, and tRNAs, or components required for transcription and translation systems. Specific examples thereof include cell extracts from *Escherichia coli*, wheat germs, tobacco cells, rabbit reticulocytes, mouse L-cells, Ehrlich ascites cancer cells, HeLa cells, CHO cells, budding yeasts and the like.

As the cell extract, cell extracts derived from *Escherichia coli* are preferable for securing stability and scalability of extract preparation. Examples of the cell extract derived from *Escherichia coli* include S30 extract (hereinafter, also referred to as "*E. coli* S30 extract"), S12 extract, etc. from *Escherichia coli* (BL21, etc.) cells. *E. coli* S30 extract contains all enzymes and factors of *Escherichia coli*, which are required for transcription and translation.

The method for preparing the cell extract is not particularly limited, and a known method can be adopted. For example, *E. coli* S30 extract can be prepared by the method described in Zubay G., Ann Rev Genet, (1973) 7, 267-287, Seki, E., Matsuda, N., Yokoyama, S., and Kigawa, T. (2008), Anal. Biochem. 377, 156-161.

Specifically, as a method for preparing a cell extract, *Escherichia coli* is first cultured, and the cells are recovered by centrifugation or the like. After washing the recovered cells, the cells are resuspended in a buffer solution and crushed using a French press, glass beads, a waring blender, or the like. The insoluble fraction of the crushed *Escherichia coli* is removed by centrifugation, and the resulting is mixed with a pre-incubation mixture and incubated. The endogenous nucleic acids (DNA, RNA) are degraded by this operation, but the endogenous nucleic acids may be further degraded by adding a calcium salt, a micrococcal nuclease, or the like. Subsequently, the endogenous amino acids, nucleic acids, nucleosides, etc. are removed by dialysis, and appropriate amounts are dispensed and stored in liquid nitrogen or stored at −80° C.

As the cell extract, a commercially available product may be used.

The amount of the cell extract in the reaction solution is preferably 40 to 200, and more preferably 50 to 150, in terms of the final concentration in the reaction solution (calculated from the absorbance at 260 nm (A260) of the cell extract). When the amount of the cell extract is within the above range, it is easy to synthesize the target protein with high efficiency.

The cell extract contains all the enzymes and factors required for transcription and translation, but additional supplemental components may be added when used in the reaction solution for the protein synthesis.

Examples of the supplemental component include substrate L-amino acids, energy sources, salts, various ions, buffers, energy regeneration systems, nuclease inhibitors, reducing agents, and antibacterial agents.

Examples of the L-amino acid include 20 kinds of natural amino acids or derivatives thereof. For producing an isotope-labeled protein as the target protein, a labeled amino acid which is labeled with a stable isotope or a radioisotope is used.

Examples of the energy source include adenosine triphosphate (ATP), cytidine triphosphate (CTP), guanosine triphosphate (GTP), uridine triphosphate (UTP) (hereinafter, these four are collectively referred to as NTP), creatine phosphate (CP), phosphoenolpyruvate (PEP), and glucose. Alternatively, adenosine monophosphate (AMP), cytidine monophosphate (CMP), guanosine monophosphate (GMP), and uridine monophosphate (UMP) (hereinafter, these four are collectively referred to as NMP) may be added to the reaction solution instead of NTP, and a metabolic enzyme is exploited to allow NTP to be synthesized in the system (Calhoun K A and Swartz J R, Biotechnol. Prog., 2005, 21, 1146-1153).

Examples of the salt include ammonium acetate, potassium acetate, potassium glutamate, magnesium acetate, magnesium chloride, potassium acetate and calcium chloride.

Examples of the buffer solution include Tris-acetic acid and HEPES-KOH.

As the energy regeneration system, an ATP regeneration system is preferable. The ATP regeneration system may be, for example, a combination of 10 to 100 mM of CP and 0.02 to 5 μg/μL of creatine kinase (CK), or a combination of 1 to 20 mM of PEP and 0.01 to 1 μg/μL of pyruvate kinase (PK). Both PK and CK are enzymes that regenerate ADP into ATP and require PEP and CP as substrates, respectively.

Examples of the nuclease inhibitor include RNase inhibitors.

Examples of the reducing agent include dithiothreitol (DTT).

Examples of the antibacterial agent include sodium azide and ampicillin.

Polyethylene glycol (PEG), folic acid, cAMP, tRNA and the like may be added to the reaction solution for the purpose of enhancing protein synthesis activity. When a DNA is used as a template for the target protein, NTP as a substrate for the RNA synthesis or a precursor thereof, an RNA polymerase and the like may be added to the reaction solution. Examples of the precursor of NTP include NMP, a nucleoside and the like. Examples of the RNA polymerase include T7 RNA polymerase, T3 RNA polymerase, SP6 RNA polymerase and the like. Chaperone proteins or disulfide-bond isomerases, which help proteins to form three-dimensional structures, may be added to the reaction solution. Examples of the chaperone proteins include DnaJ, DnaK, GroE, GroEL, GroES, HSP70 and the like. Examples of the disulfide-bond isomerase include DsbC and the like.

With respect to such supplementary components, a single type thereof may be used alone or two or more types thereof may be used.

When *E. coli* S30 extract is used, the reaction solution preferably contains *E. coli* S30 extract. L-amino acids, a buffer solution, a salt, NTP, and an energy source. For example, the reaction solution may be one containing *E. coli* S30 extract, HEPES-KOH, DTT, NTP (ATP, CTP, GTP, UTP), CP, CK, and at least one amino acid (selected from 20 natural amino acids or derivatives thereof).

The supplemental component is preferably stored separately from the cell extract and mixed immediately before use. It is also possible to premix the supplemental component with the cell extract and freeze-thaw the mixture to remove the RNase complex (International Publication No. 2000/183805).

In the present invention, the reaction solution for the cell-free protein synthesis system contains either one or both of a Csp and a Csp template nucleic acid. In the present invention, it is preferable to use a Csp.

A Csp is thought to be involved in adaptation to low temperature environments, and has been found in wide variety of organisms ranging from bacteria to higher animals and plants. Examples of the Csp include CspA, CspB, CspC, CspE, CspG and CspI, each derived from *Escherichia coli*, SliCspC derived from *Shewanella livingstonensis* of the genus *Shewanella*, and BsuCspB derived from *Bacillus subtilis* of the genus *Bacillus*. The CspA derived from *Escherichia coli* is the most prominently expressed Csp in a low temperature environment. The Csp is preferably a wild-type CspA or a wild-type SliCspC. The Csp contained in the reaction solution may be of one type or two or more types.

Table 1 shows the score values ($S_P$ values) of the respective proteins or protein domains relative to the CSD family (PF00313) of the Pfam database (version 32.0). The $S_P$ value of the Csp to be used is not limited as long as the value is 100 or more, and the higher the value, the easier it is to obtain the effect of producing an active protein with high efficiency even at a low temperature. The upper limit of the S$_p$ value of the Csp is not particularly limited but may be, for example, 115 in terms of availability.

TABLE 1

| Csp | Sp value |
| --- | --- |
| CspE | 114.4 |
| CspC | 113.4 |
| CspG | 113.4 |
| CspA | 111.9 |
| CspB | 107.8 |
| CspI | 107.0 |
| BsuCspB | 103.3 |
| SliCspC | 102.0 |

When the Csp is used, the amount of Csp in the reaction solution is preferably 0.5 to 1.5 μg/μL. When the reaction temperature is at 16 to 23° C., the amount of Csp is more preferably 0.8 to 1.2 μg/μL, and when the reaction temperature is lower than 16° C., the amount of Csp is more preferably 1.2 to 1.5 μg/μL. When the amount of the Csp is within the above range, the target protein can be easily synthesized with high efficiency.

The method for adjusting the amount of Csp in the reaction solution is not particularly limited. For example, the amount of Csp can be adjusted to the above range by adding Csp to the reaction solution. Alternatively, the amount of Csp may be adjusted as follows. Using cells capable of expressing Csp as cells for preparing a cell extract, a cell extract containing Csp is obtained by applying a low temperature shock during culturing. The obtained cell extract containing Csp is used to adjust the amount of Csp in the reaction solution to fall within the above range. Further, the amount of Csp in the reaction solution may also be adjusted as follows. A plasmid template DNA for Csp expression is transformed into cells for preparing a cell extract, and a cell extract containing Csp, obtained by culturing the cells, is used to adjust the amount of Csp in the reaction solution to fall within the above range.

The Csp template nucleic acid is a nucleic acid that serves as a template for synthesizing a Csp in a cell-free protein synthesis system. The presence of the Csp template nucleic acid in the reaction solution of the cell-free protein synthesis system allows a Csp to be synthesized during the reaction, whereby a reaction solution containing the Csp is obtained. Since a Csp is rapidly synthesized even in a low temperature environment, the target protein is synthesized in the presence of a Csp even when a Csp template nucleic acid is used. The Csp template nucleic acid contained in the reaction solution may be of one type or two or more types.

When the Csp template nucleic acid is used, the amount of the Csp template nucleic acid in the reaction solution is preferably 0.1 to 1.0 ng/μL, more preferably 0.2 to 0.8 ng/μL, and even more preferably 0.2 to 0.4 ng/μL. When the amount of the Csp template nucleic acid is within the above range, the target protein can be easily synthesized with high efficiency.

In the present invention, a template DNA encoding the amino acid sequence of the target protein may be added to the cell-free transcription-translation system to synthesize the target protein, and a template RNA encoding the amino acid sequence of the target protein may be added to the cell-free translation system to synthesize target protein.

The template DNA of the target protein may be either a circular double-stranded DNA such as a plasmid DNA prepared by recombinant DNA technology or a linear DNA prepared by PCR. In the present invention, the target protein can be synthesized stably and with high efficiency even by using a linear template DNA.

The amount of the template DNA or the template RNA in the reaction solution can be appropriately chosen depending on the protein synthesis activity of the cell extract, the type of the target protein, and the like, and may be, for example, about 0.5 to 10 μg/mL.

Examples of the protein synthesis method applicable in the present invention includes a dialysis method, a batch method, and a multi-layer method (Sawasaki, T., Hasegawa, Y., Tsuchimochi, M., Kamura, N., Ogasawara, T., Kuroita, T. and Endo, Y. (2002) FEBS Lett. 514, 102-10.5), of which the dialysis method is preferable.

The dialysis method is a method in which an internal solution as a reaction solution and an external solution containing a reaction substrate are separated by a dialysis membrane (ultrafiltration membrane) and the synthesis is carried out in a closed system that can be shaken or stirred. In the dialysis method, the substrate required for synthesis is supplied from the external solution to the reaction solution through the dialysis membrane, while allowing unnecessary by-products in the reaction solution to diffuse into the external solution, whereby the reaction can be sustained for a longer period of time. Therefore, the protein can be synthesized in a higher yield.

The reaction temperature is preferably 4 to 30° C., and more preferably 16 to 23° C. The reaction time for the batch method is preferably 2 to 6 hours, and more preferably 4 to 6 hours when the reaction temperature is not higher than 16° C. The reaction time for the dialysis method is preferably 1 to 40 hours, and more preferably 5 to 40 hours.

The molecular weight cut-off of the dialysis membrane that separates the internal dialysis solution and the external dialysis solution is preferably 3,500 to 100,000, and more preferably 10,000 to 50,000.

The shaking speed or stirring speed may be, for example, 100 to 300 rpm.

The synthesized target protein is preferably subjected to purification. As a method for purifying the target protein, a known method for purifying proteins can be adopted, and examples thereof include ammonium sulfate precipitation, acetone precipitation, acid extraction, anion exchange chromatography, cation exchange chromatography, hydrophobic interaction chromatography, affinity chromatography, gel filtration chromatography, hydroxyapatite chromatography, isoelectric point chromatography, chromatofocusing and the like. With respect to these purification methods, a single type thereof may be implemented individually or two or more types thereof may be implemented in combination. Further, an affinity purification method may be used in which a tag is added to the target protein at the time of synthesis and an adsorbent that specifically recognizes the tag is used. Examples of the tag include a histidine tag, a GST tag, a maltose-binding tag, and the like.

The identification and quantification of the target protein can be performed by activity measurement, immunological measurement, spectroscopic measurement, amino acid analysis or the like, while, if necessary, comparing with a reference sample.

The use of the protein produced by the protein production method of the present invention is not particularly limited. For example, the protein can be used for X-ray crystal analysis, three-dimensional structure analysis by NMR measurement, enzyme activity measurement, and the like. Since the method of the present invention can produce the target protein with high efficiency while suppressing precipitation and inactivation at a low temperature, it is suitable to use the protein for the three-dimensional structure analysis and the enzyme activity measurement, which require a large amount of protein.

[Cell-Free Protein Synthesis Kit]

The cell-free protein synthesis kit of the present invention includes either one or both of a Csp and a Csp template nucleic acid, and a reaction solution for the cell-free protein synthesis system.

In the cell-free protein synthesis kit of the present invention, the Csp and the Csp template nucleic acid may be mixed in advance or may be provided separately from the cell extract. Further, the kit may have a configuration in which the supplementary component to be used in the reaction solution is provided separately from the cell extract and is supposed to be mixed with the cell extract immediately before use. Instead of the cell extract, a solution used for the above-mentioned reconstituted cell-free protein synthesis method may be provided.

In the cell-free protein synthesis kit, the components are dispensed in predetermined amounts for easy use. The components can be stored frozen or dried, and are contained in a container suitable for storage and transportation to form a kit. An instruction manual, positive control DNAs vector DNAs, etc. may be attached to the kit.

As described above, in the present invention, the target protein is produced using a reaction solution of a cell-free protein synthesis system containing either one or both of a Csp and a Csp template nucleic acid. The presence of the Csp in the reaction solution of the cell-free protein synthesis system enables highly efficient production of an active target protein even at low temperatures. The factors leading to such an effect are not necessarily clear, but the conceivable factors are the suppression of degradation of mRNA in the reaction solution, the suppression of formation of higher-order structure of mRNA, etc.

Hereinbelow, the present invention will be described with reference to Examples which, however, should not be construed as limiting the present invention.

Example 1 CspA Concentration Dependence of GFP Protein Synthesis

As *E. coli* S30 extract, an enzyme solution for stable isotope-labeled cell-free synthesis (manufactured by Taiyo Nippon Sanso Corporation) prepared from *E. coli* BL21 codon plus strain was used. LMCP (D-Glu)-tRNA (manufactured by Taiyo Nippon Sanso Corporation) was used as a reagent for protein synthesis excluding enzymes and amino acids.

As a template DNA for GFP protein, pCR2.1-N11-GFPS1 which is a plasmid DNA was used. This plasmid is composed of a T7 promoter, a ribosome binding sequence, a His tag sequence for affinity purification, a GFP protein variant (GFPS1) gene, and a T7 terminator (Seki, E., Matsuda, N., Yokoyama, S., and Kigawa, T. (2008), Anal. Biochem. 377, 156-161, [Anal. Biochem. 517, (2017), 22]).

In the protein synthesis reaction, a reaction solution having the composition shown in Table 2 below was dialyzed against a dialysis external solution having the composition shown in Table 3, and the reaction was implemented at 4° C., 8° C., 12° C., 16° C., 20° C., 23° C. and 30° C. for 18 hours. With regard to the scale of reaction, the amount of the internal solution (reaction solution) was 30 μL, and the amount of the dialysis external solution was 500 μL. A purified CspA derived from *E. coli* ($S_P$ value: 111.9) was added to the reaction solution so as to give various concentrations in the range of 0 to 1.5 μg/μL, and the reaction was implemented. The purified CspA was synthesized by a cell-free protein synthesis system.

Further, "LMCP (D-Glu)-tRNA" in Tables 2 and 3 refers to a mixture of HepesKOH (pH 7.5) as a buffer solution, D-potassium glutamate and ammonium acetate as salts, ATP as an energy source, GTP, CTP and UTP as transcription substrates, and cyclic AMP, folic acid, DTT and polyethylene glycol as other reagents.

TABLE 2

| Composition of internal solution | Concentration |
|---|---|
| LMCP(D-Glu)-tRNA | 37.3 vol % |
| *E. coli* total tRNA | 175 ng/μL |
| Sodium azide | 0.05 vol % |
| Magnesium acetate | 6 to 8 mM |
| L-amino acid (20 types) | 1.5 mM each |
| Creatine Kinase | 0.25 mg/mL |
| T7 RNA polymerase | 66.6 μg/mL |
| *E. coli* S30 extract (A260 of S30 extract = 228) | 30 vol % |
| Template DNA (expression vector: pCR2.1-N11-GFPS1) | 1 to 2 ng/μL |

TABLE 3

| Composition of dialysis external solution | Concentration |
|---|---|
| LMCP(D-Glu)-tRNA | 37.3 vol % |
| Sodium azide | 0.05 vol % |
| Magnesium acetate | 6 to 8 mM |
| Amino acids (20 types) | 1.5 mM each |
| S30 buffer | 30 vol % |

The total fraction after the reaction was subjected to SDS (sodium dodecyl sulfate)-polyacrylamide gel electrophoresis containing 15% tricine (15% Tricine-SDS-PAGE), and then stained with CBB. The results are shown in FIG. 1.

The yield of the synthesized GFPS1 is shown in terms of the fluorescence intensity of GFPS1. After diluting the reaction solution with a buffer solution (20 mM Tris-HCl, pH 7.5, 300 mM NaCl), the fluorescence intensity of GFPS1 was measured at an excitation of 485 nm and a fluorescence of 535 nm using a multimode microplate reader SpectraMax i3 (manufactured by Molecular Devices). The results are shown in FIG. 2.

Figure 3:
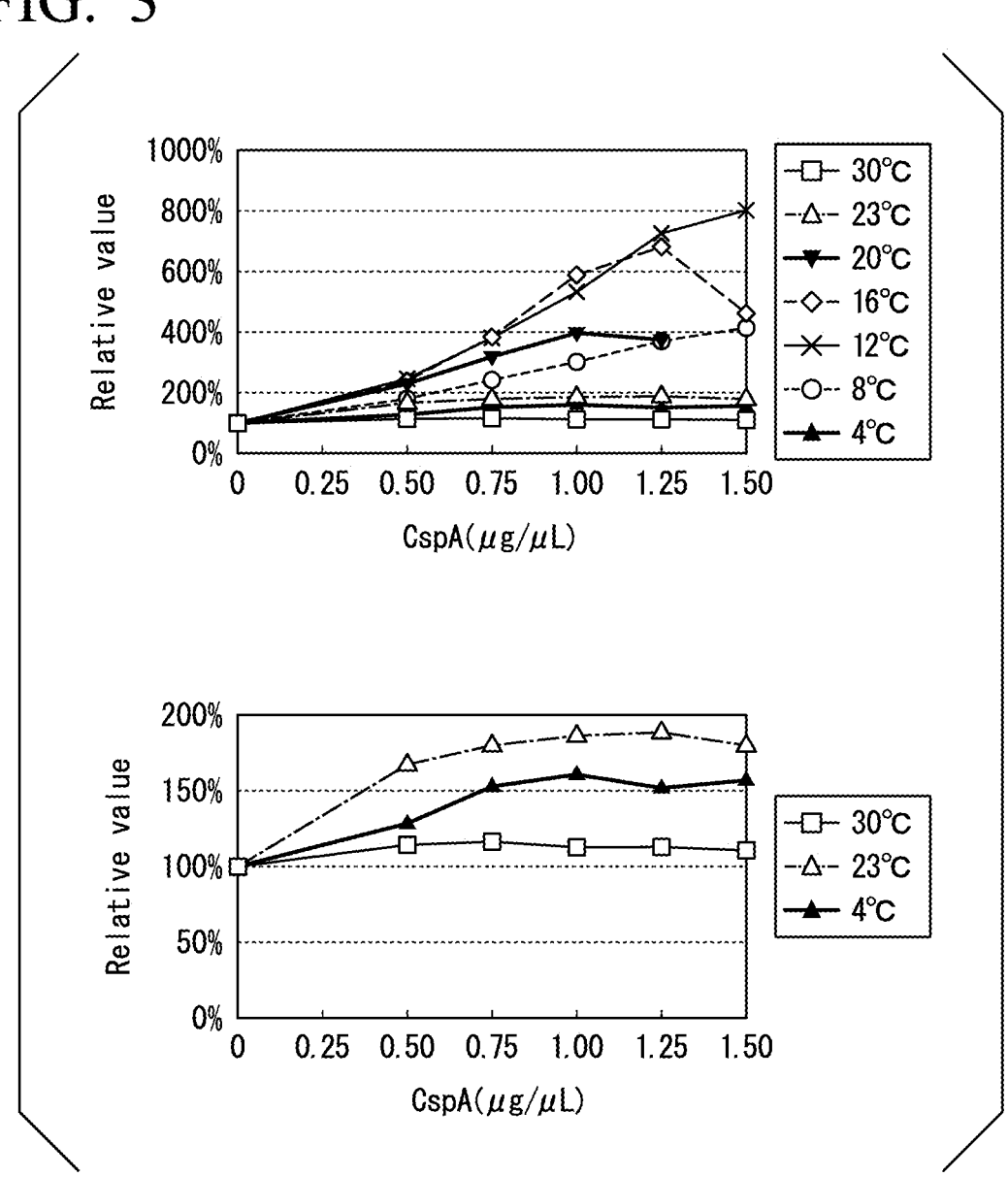
FIG. 3 is a diagram showing the CspA concentration dependence of the yield of GFPS1 synthesized in Example 1.

Further, FIG. 3 shows the CspA concentration dependence in terms of the relative value of the yield of GFPS1 based on the yield of GFPS1 synthesized in the absence of the CspA.

Figure 2:
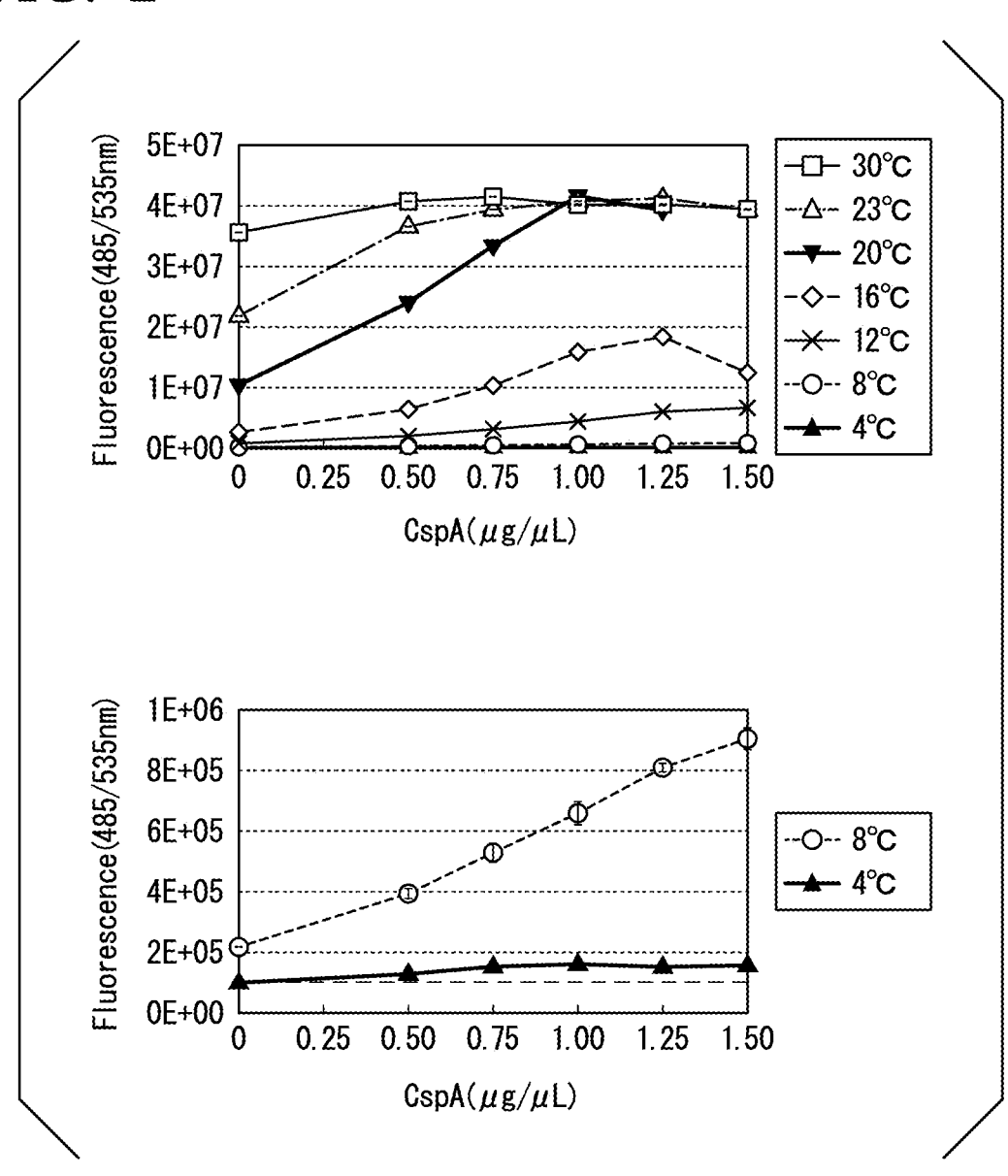
FIG. 2 is a diagram showing the yield (fluorescence intensity) of GFPS1 synthesized in Example 1.

As shown in FIG. 1 to FIG. 3, in the reactions implemented at 4° C. to 23° C., the yield of GFPS1 increased as the concentration of CspA increased, and the level of the yield increase was higher as compared to the case of the reaction implemented at 30° C. The reaction implemented at a reaction temperature of 23° C. and with the addition of CspA in an amount (CspA content) of 0.75 to 1.25 μg/μL, and the reaction implemented at a reaction temperature of 20° C. and with the addition of CspA in an amount of 1.0 to 1.25 μg/μL resulted in a high yield which is at the same or higher level than the reaction implemented at a reaction temperature of 30'° C. The reaction implemented at a reaction temperature of 16° C. and with the addition of CspA in an amount of 1.0 to 1.25 μg/μL, and the reaction implemented at a reaction temperature of 12° C. and with the addition of CspA in an amount of 1.25 μg/μL or more resulted in a yield 6 or more times higher than the reaction implemented in the absence of CspA.

Example 2 Protein Synthesis in the Presence of CspA

Following the same procedure as in Example 1 while varying the template DNA, CAT (template DNA: pUC-CAT), hAK1 (template DNA: pCR2.1-NHis-hAK1), hPGK (template DNA: pCR2.1-N11-hPGK), and GFPS1 (template DNA: pCR2.1-N11-GFPS1) were synthesized as proteins at a reaction temperature of 20° C. in the presence and absence of CspA (1.0 μg/μL).

After the reaction, the total fraction (T) and the soluble fraction (S) of the reaction solution were subjected to 15% Tricine-SDS-PAGE and then stained with CBB. The results are shown in FIG. 4.

Figure 4:
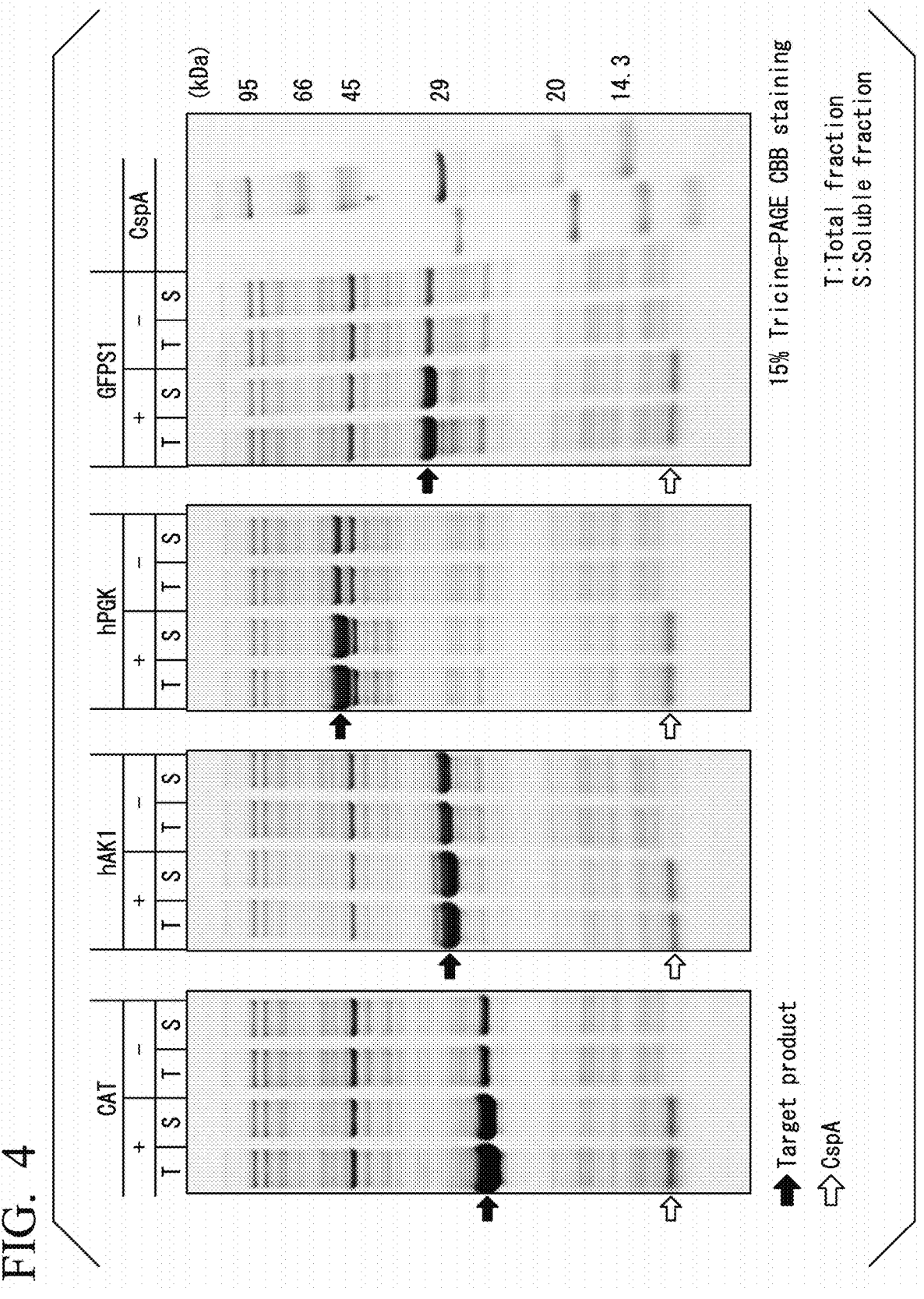
FIG. 4 shows the electrophoresis results with respect to the total fraction (T) and the soluble fraction (S) after the synthesis reaction of each protein in Example 2.

FIG. 4 reveals that not only GFPS1 but also other proteins were synthesized in higher yield in the reaction implemented in the presence of CspA as compared to the reaction implemented in the absence of CspA.

Example 3 Improvement of Solubility of Precipitation-Prone Protein

Following the same procedure as in Example 2, hAK1 was synthesized at a reaction temperature of 20° C. or 30° C. After the reaction, the total fraction (T) and the soluble fraction (S) of the reaction solution were subjected to 15% Tricine-SDS-PAGE and then stained with CBB. The results are shown in FIG. 5.

Figure 5:
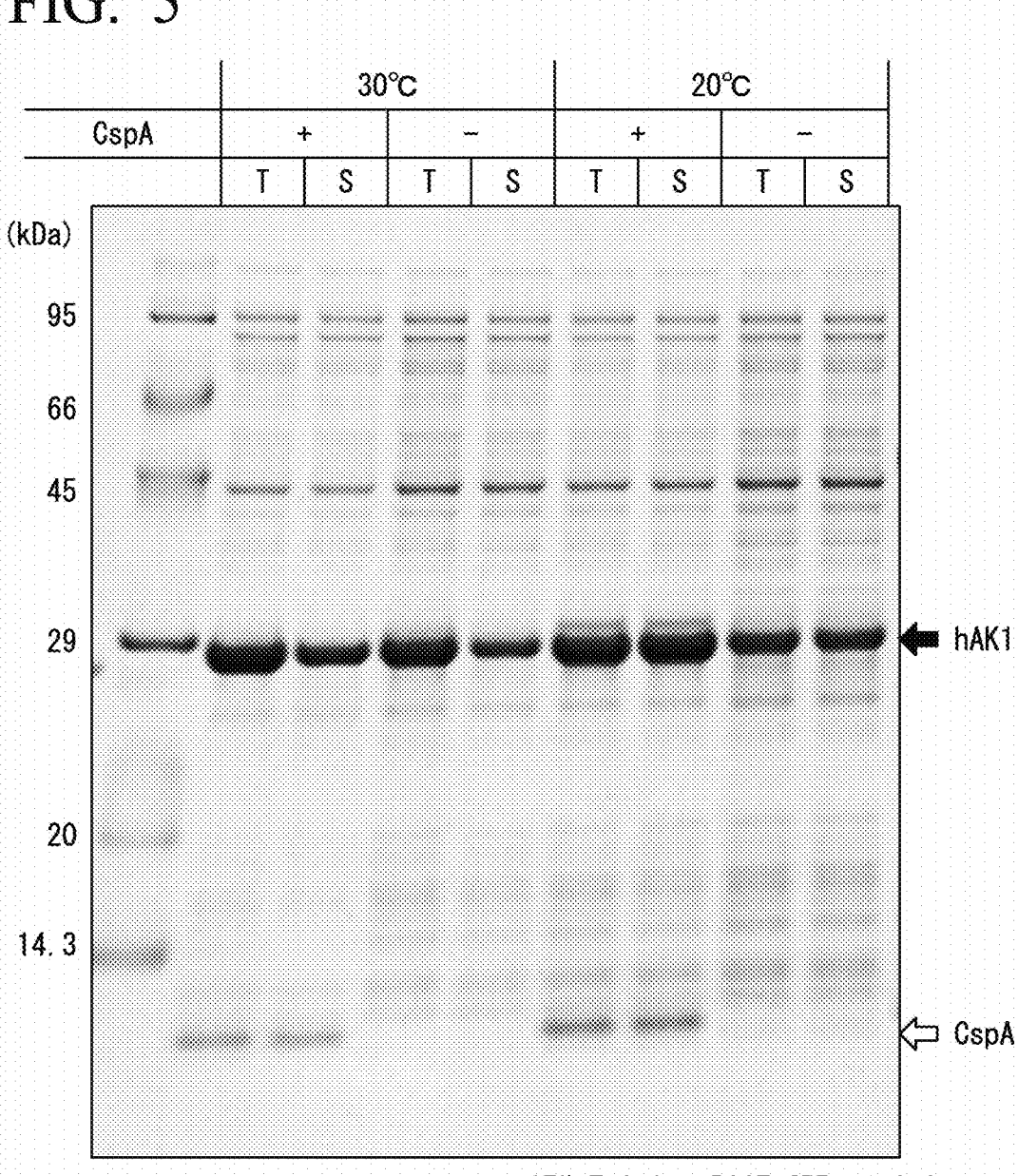
FIG. 5 shows the electrophoresis results with respect to the total fraction (T) and the soluble fraction (S) after the synthesis reaction of hAK1 in Example 3.

As shown in FIG. 5, even in the case of hAK1 which is highly prone to precipitation when synthesized at a reaction temperature of 30° C., the precipitation was suppressed with the reaction temperature of 20° C. In addition, the reaction implemented in the presence of CspA showed an increase in the protein yield while maintaining high solubility.

Example 4 Protein Synthesis Using Csp (CSD) Other Than CspA

Many proteins with high amino acid sequence identity with CspA are known. Although CspA has the ability to bind to nucleic acids, there are also CspA homologs that do not bind to nucleic acids. Using such CspA homologs, GFPS1 was synthesized following the same procedure as in Example 1. Specifically, GFPS1 was synthesized following the same procedure as in Example 1 at 23° C. using *E. coli*-derived CspA, CspB (S$_P$ value: 107.8), CspC (S$_P$ value: 113.4), CspD (S$_P$ value: 99.5), CspE (S$_P$ value: 114.4), CspG (S$_P$ value: 113.4), CspH (S$_P$ value: 79.4), CspI (S$_P$ value: 107.0), human-derived hCSDE1-CSD1 (S$_P$ value: 61.7), *Shewanella livingstonensis*-derived SliCspC (S$_P$ value: 102.0), *Arabidopsis thaliana*-derived AtCSP3-CSD (S$_P$ value: 83.7), and *Bacillus subtilis*-derived BsuCspB (S$_P$ value: 103.3).

The fluorescence intensity of GFPS1 was measured in the same manner as in Example 1. The Csp concentration dependence of the yield of GFPS1 is shown in FIG. 6.

Figure 6:
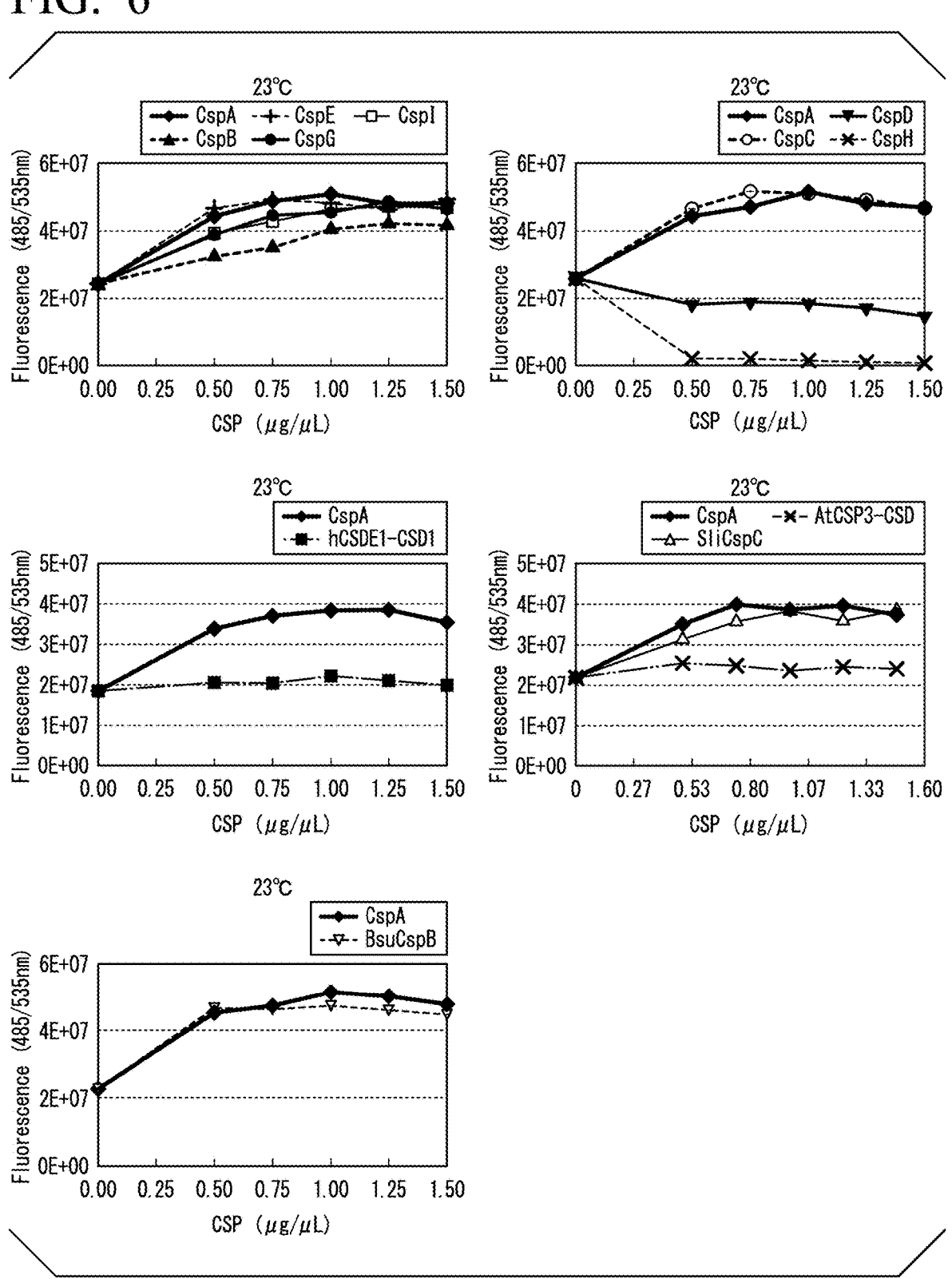
FIG. 6 is a diagram showing the Csp (CSD) concentration dependence of the yield of GFPS1 synthesized in Example 4.

As shown in FIG. 6, it was found that CspB, CspC, CspE, CspG and CspI, each derived from *Escherichia coli*, SliCspC derived from *Shewanella livingstonensis*, and BsuCspB derived from *Bacillus subtilis* have the same action as CspA derived from *Escherichia coli*.

Example 5 Protein Synthesis at Various Reaction Temperatures

Following the same procedure as in Example 1, GFPS1 and CAT were synthesized with reaction temperatures of 16°

C., 23° C., 30° C. and 37° C. in the presence and absence of CspA (addition amount: 1.0 μg/μL).

As a template DNA for CAT, pk7-CAT (Kim D M, Kigawa T, Choi C Y, Yokoyama S (1996) Eur J Biochem 239: 881-886) was used. The yield of CAT protein synthesized was determined through conversion following the method of Kigawa et al. (Kigawa T, Yabuki T, Matsuda N, Matsuda T, Nakajima R, Tanaka A, Yokoyama S. (2004) J Struct Funct Genomics 5, 63-68).

Figure 7:
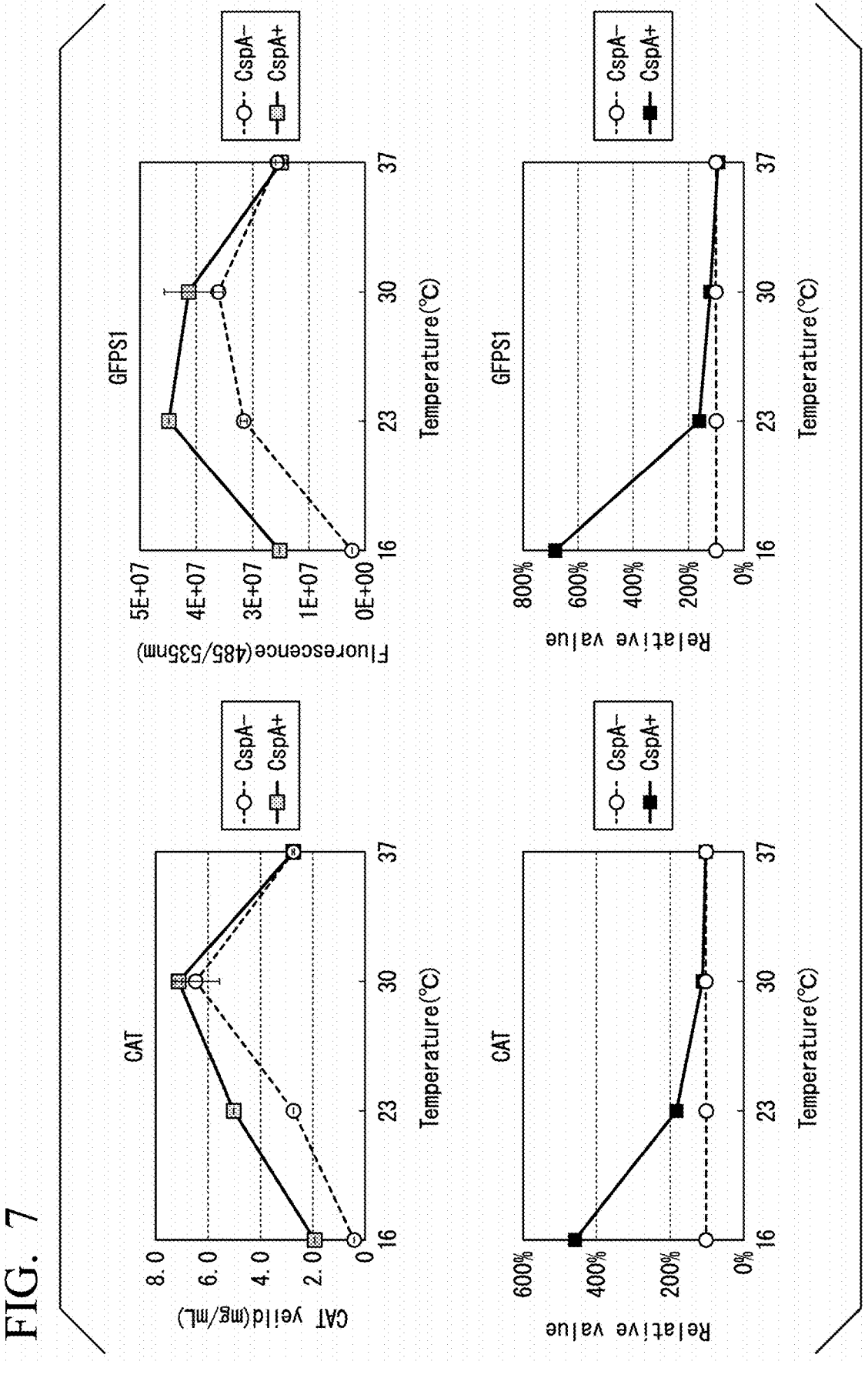
FIG. 7 is a diagram showing the reaction temperature dependence of the yields of GFPS1 and CAT synthesized in Example 5.

FIG. 7 shows the reaction temperature dependence of the yields of GFPS1 and CAT synthesized in the presence of CspA (CspA+) and in the absence of CspA (CspA−).

FIG. 7 reveals that, as the reaction temperature decreased, both proteins, GFPS1 and CAT, were synthesized in much higher yields in the reaction implemented in the presence of CspA as compared to the reaction implemented in the absence of CspA. Each of the relative values in FIG. 7 is a ratio of the yield of synthesis implemented in the presence of CspA (CspA+) relative to the yield of synthesis implemented in the absence of CspA (CspA−).

Example 6 Protein Synthesis at Various Reaction Temperatures

GFPS1 and CAT were synthesized with employing a batch method as the synthesis method instead of the dialysis method employed in the previous Examples, using a solution having the composition shown in Table 4 below as the reaction solution, and with a reaction time of 4 hours and reaction temperatures of 16° C., 23° C., 30° C. and 37° C. in the presence or absence of CspA (addition amount: 1.0 μg/μL). As a template DNA for CAT, the same DNA as in Example 5 was used.

Figure 8:
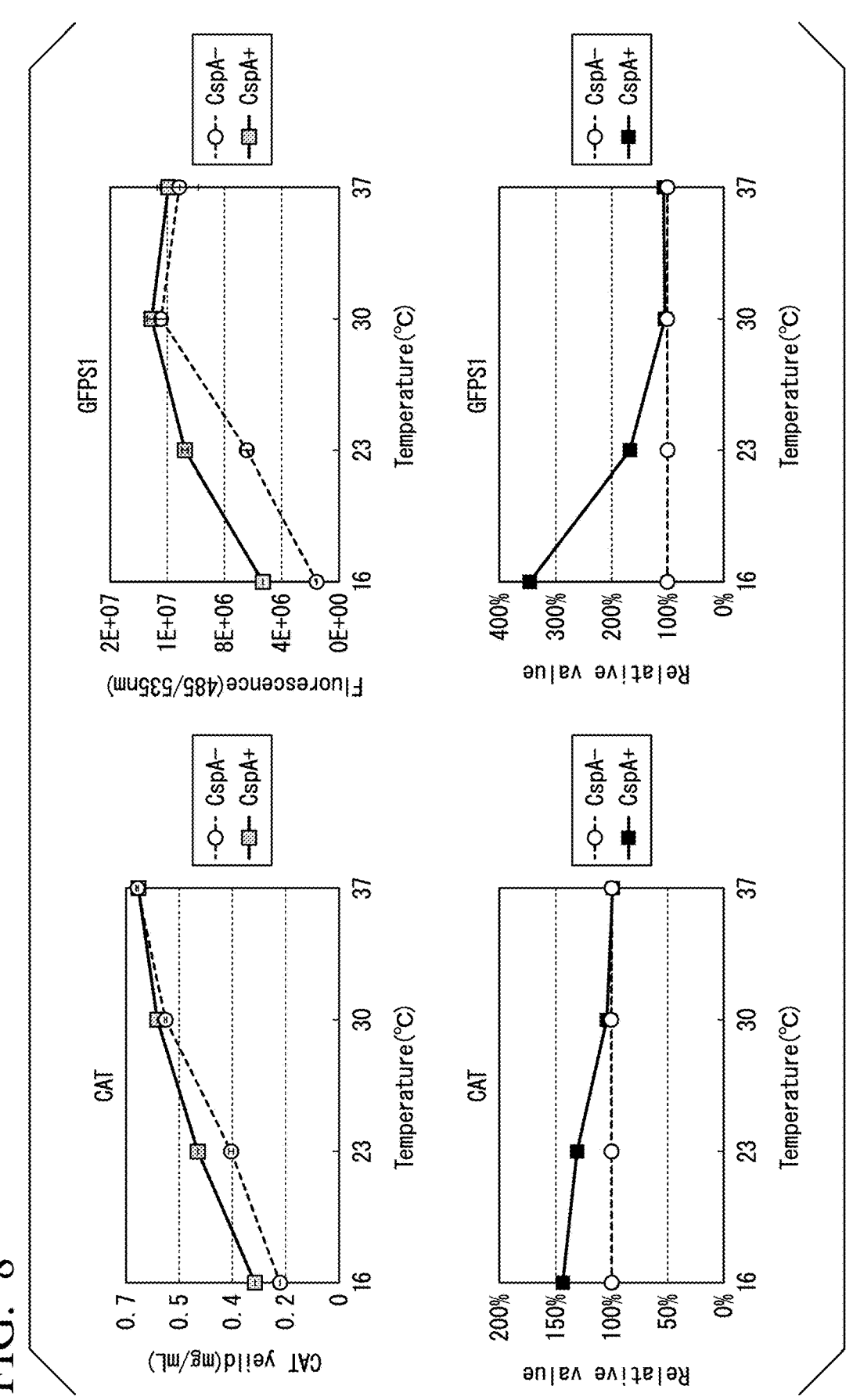
FIG. 8 is a diagram showing the reaction temperature dependence of the yields of GFPS1 and CAT synthesized in Example 6.

FIG. 8 shows the reaction temperature dependence of the yields of GFPS1 and CAT synthesized in the presence of CspA (CspA+) and in the absence of CspA (CspA−). Each of the relative values in FIG. 8 is a ratio of the yield of synthesis implemented in the presence of CspA (CspA+) relative to the yield of synthesis implemented in the absence of CspA (CspA−).

TABLE 4

| Composition of reaction solution | Concentration |
|---|---|
| LMCP(D-Glu)-tRNA | 37.3 vol % |
| *E. coli* total tRNA | 175 ng/μL |
| Magnesium acetate | 5 to 13 mM |
| L-amino acid (20 types) | 1.5 mM each |
| Creatine Kinase | 0.25 mg/mL |
| T7 RNA polymerase | 133 μg/mL |
| *E. coli* S30 extract (A260 of S30 extract = 228) | 24 vol % |
| Template DNA (expression vector: pCR2.1-N11-GFPS1) | 4 ng/μL |

FIG. 8 reveals that even in the case of the batch method, as the reaction temperature decreased, both proteins, GFPS1 and CAT, were synthesized in much higher yields in the reaction implemented in the presence of CspA as compared to the reaction implemented in the absence of CspA.

Example 7 Change Over Time in the Yield of GFPS1 Synthesized at Various Reaction Temperatures Following the same procedure as in Example 1, GFPS1 was synthesized with reaction temperatures of 16° C., 23° C.

and 30° C. and reaction times within 0 to 40 hours in the presence and absence of CspA (addition amount: 1.0 μg/μL).

Figure 9:
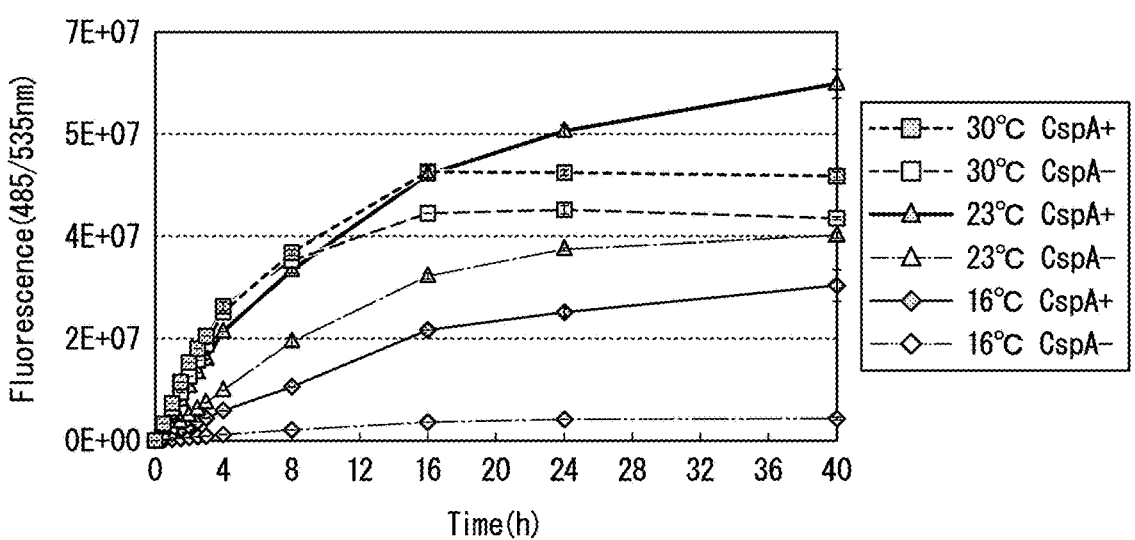
FIG. 9 is a diagram showing the change over time in the yield of GFPS1 synthesized at respective reaction temperatures in Example 7.

The fluorescence intensity of GFPS1 was measured in the same manner as in Example 1. FIG. 9 shows the change over time in the yield of GFPS1 synthesized at the respective reaction temperatures in the presence of CspA (CspA+) and in the absence of CspA (CspA–).

As shown in FIG. 9, the protein synthesis implemented in the presence of CspA was sustained for a longer period of time than that implemented in the absence of CspA. Moreover, while the synthesis reaction at 30° C. stopped at 16 hours, the synthesis reaction at 23° C. in the presence of CspA continued for up to 40 hours and, hence, resulted in a final yield of protein which greatly exceeds the yield in the synthesis reaction at 30° C.

Example 8 GFPS1 Protein Synthesis in the Presence of CspA Template DNA

Following the same procedure as in Example 1, GFPS1 was synthesized with 10 mM of magnesium acetate, a reaction temperature of 23° C., and a reaction time of 18 hours. The reaction was carried out by adding a CspA template DNA to the reaction solution so as to give various concentrations thereof in the range of 0 to 0.8 ng/μL. The CspA template DNA used was a linear N11-CspA composed of a T7 promoter, a ribosome binding sequence, a His tag sequence for affinity purification, a CspA protein gene (gene containing a coding region encoding the amino acid sequence of CspA ($S_P$ value: 111.9) derived from *Escherichia coil*) and a T7 terminator.

Figure 10:
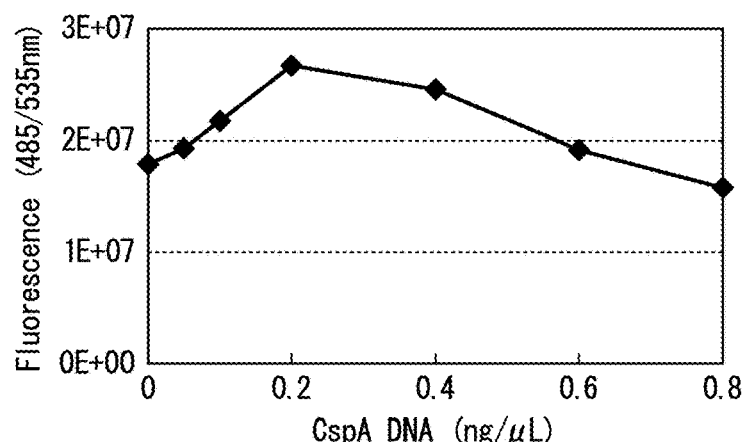
FIG. 10 is a diagram showing the yield (fluorescence intensity) of GFPS1 synthesized in Example 8.

The fluorescence intensity of GFPS1 was measured in the same manner as in Example 1. The results are shown in FIG. 10. Further, FIG. 11 shows the CspA-template DNA concentration dependence in terms of the relative value of the yield of GFPS1 based on the yield of GFPS1 synthesized in the absence of the CspA.

Figure 11:
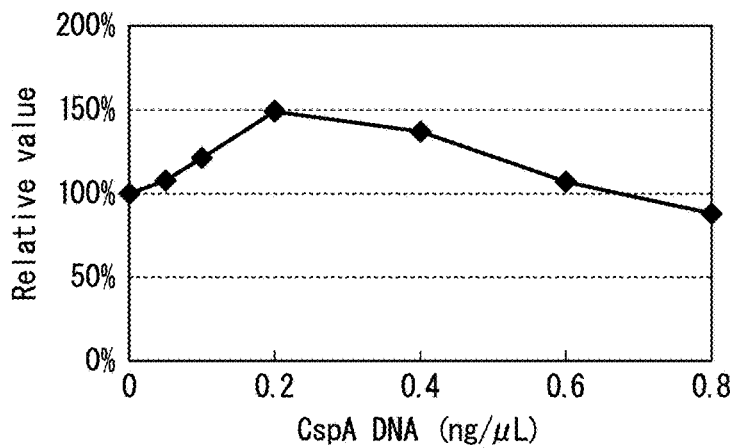
FIG. 11 is a diagram showing the CspA-template DNA concentration dependence of the yield of GFPS1 synthesized in Example 8.

As shown in FIG. 10 to FIG. 11, in the reaction implemented at 23° C., the yield of GFPS1 increased as the concentration of CspA template DNA increased, and gradually decreased when the amount added exceeded 0.4 ng/μL. When the amount of CspA template DNA added was in the range of 0.2 to 0.4 ng/μL, the yield of GFPS1 was about 1.5 times higher than the reaction implemented in the absence of CspA.

Example 9 Improvement of Solubility of Human-Derived Protein

Following the same procedure as in Example 5, proteins were synthesized at a reaction temperature of 16° C. or 30° C. from the genes of human-derived proteins cloned from Human Universal QUICK-Clone™ cDNA II (Clontech), i.e., TRIB2 (template DNA: pCR2.1-N11-TRIB2), CASP7 (template DNA: linear N11-CASP7) MAP2K6 (template DNA: linear N11-MAP2K6) AURKB (template DNA: linear N11-AURKB).

After the reaction, the total fraction (T) and the soluble fraction (S) of the reaction solution were subjected to 15% Tricine-SDS-PAGE and then stained with CBS. The results are shown in FIG. 12.

Figure 12:
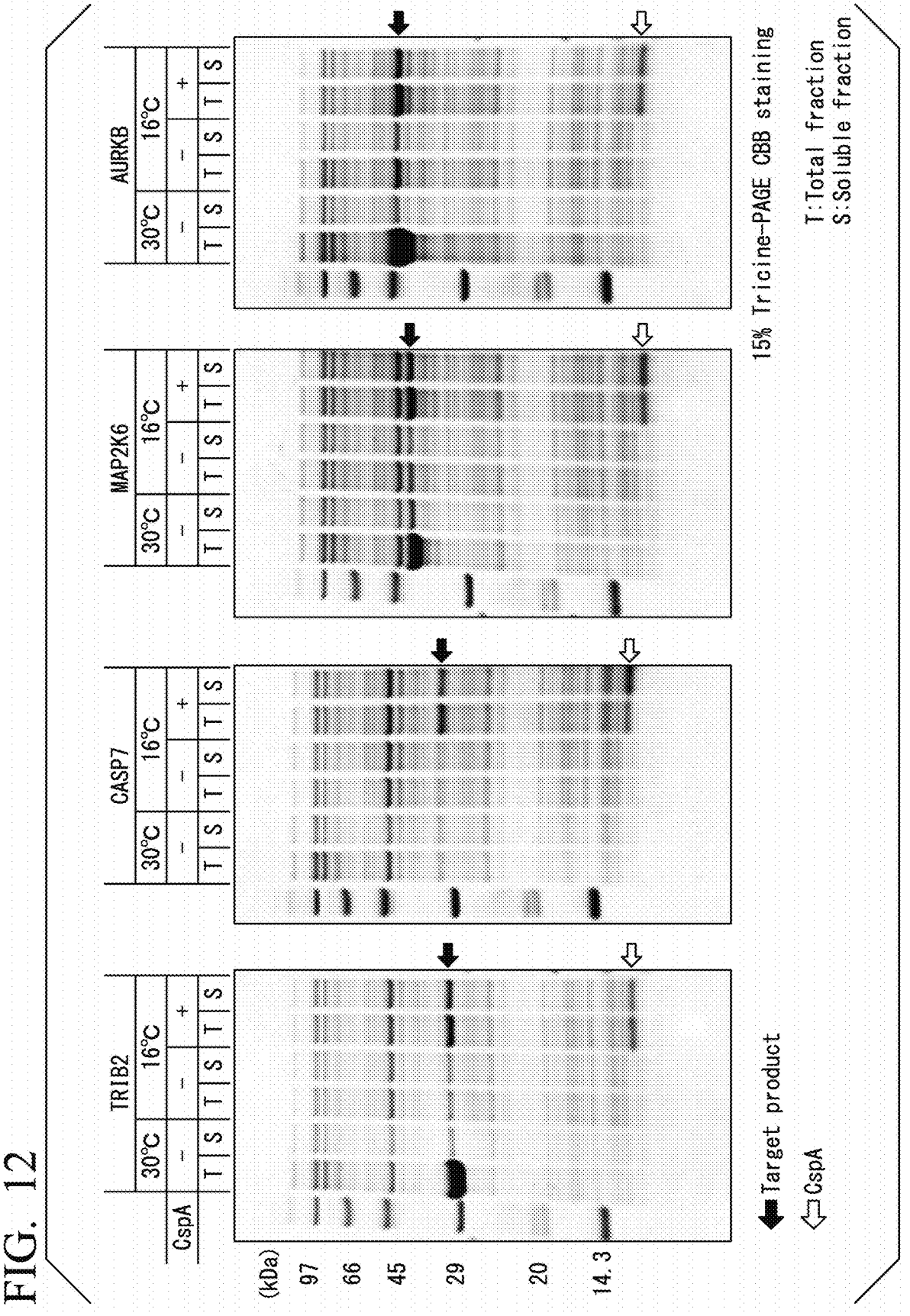
FIG. 12 shows the electrophoresis results with respect to the total fraction (T) and the soluble fraction (S) after the synthesis reaction of each protein in Example 9.

As shown in FIG. 12, even in the synthesis of human cDNA-derived proteins which are highly prone to precipitation when synthesized at a reaction temperature of 30° C., precipitation was suppressed by the reaction implemented at 16° C. In addition, the reaction implemented in the presence of CspA showed an increase in the protein yield while maintaining high solubility. CASP7, which shows poor expression at 30° C., showed an increase in the protein yield in the reaction implemented at 16° C. while maintaining high solubility.

Example 10 Improvement of Solubility of Low Molecular Weight Antibody

As *E. coli* S30 extract, one prepared by replacing the solvent of a stable isotope-labeled cell-free synthetic enzyme solution (manufactured by Taiyo Nippon Sanso Corporation) prepared from the *E. coli* BL21 codon plus strain with a solvent containing no DTT by dialysis was used. As a reagent for protein synthesis excluding enzymes and amino acids, LMCP (D-Glu)-tRNA-DTT (manufactured by Taiyo Nippon Sanso Corporation) was used.

As template DNAs for single chain antibody Fv (scFv), which is a low molecular weight antibody, Cetuximab scFv (pCR2.1-N11-Cetu-VLVH-SBP), Infliximab scFv (pCR2.1-N11-Inf-VLVH-SBP), Bevacizumab scFv (pCR2.1-N11-Beva-VLVH-SBP), and Tocilizumab scFv (pCR2.1-N11-Toci-VLVH-SBP) were used to synthesize respective scFv antibodies. Each of these plasmids was composed of a T7 promoter, a ribosome binding sequence, a His tag sequence for affinity purification, a solubilized SUMO tag sequence, an antigen binding site (VL and VH) gene for each antibody, a linker sequence that links VL and VH, a SBP tag sequence for affinity purification, and a T7 terminator. Further, as template DNAs for Fab which is one of the low molecular weight antibodies, Cetuximab Fab (H chain: pCR2.1-N11-Cetu-VHCH1-SBP, L chain: pCR2.1-N11-Cetu-VLCL), Infliximab Fab (H chain: pCR2.1-N11-Inf-VHCH1-SBP, L chain: pCR2.1-N11-Cetu-VLCL), Bevacizumab Fab (H chain: pCR2.1-N11-Beva-VHCH1-SBP, L chain: pCR2.1-N11-Beva-VLCL), Tocilizumab Fab (H chain: pCR2.1-N11-Toci-VHCH1-SBP, L chain: pCR2.1-Toci-VLCL) were used, and respective Fab antibodies were synthesized by allowing coexpression of both of the gene encoding the H chain and the gene encoding the L chain. Each of the plasmids for H chains was composed of a T7 promoter, a ribosome binding sequence, a His tag sequence for affinity purification, a solubilized SUMO tag sequence, a H chain (VH, CH1) gene of each antibody, a SBP tag sequence for affinity purification, and a T7 terminator. Each of the plasmids for L chains was composed of a T7 promoter, a ribosome binding sequence, a His tag sequence for affinity purification, a L chain (VL, CL) gene of each antibody, and a T7 terminator.

In the protein synthesis reaction, a reaction solution having the composition shown in Table 5 below was dialyzed against a dialysis external solution having the composition shown in Table 6, and the synthesis was implemented at reaction temperatures of 16° C. and 23° C. for 20 hours in the presence and absence of CspA (addition amount (16° C.): 1.0 μg/μL, addition amount (23° C.): 0.67 μg/μL). Further, a synthesis reaction was also implemented in the same manner in the absence of CspA at a reaction temperature of 30° C.

TABLE 5

| Composition of internal solution | Concentration |
| --- | --- |
| LMCP(D-Glu)-tRNA-DTT | 37.3 vol % |
| *E. coli* total tRNA | 175 μg/mL |
| Sodium azide | 0.05 vol % |
| Magnesium acetate | 6 to 8 mM |

TABLE 5-continued

| Composition of internal solution | Concentration |
| --- | --- |
| L-Amino acid-DTT (20 types) | 1.0 mM |
| Reduced glutathione | 2.5 mM |
| Oxidized glutathione | 2.5 mM |
| IPTG | 0.5 mM |
| Creatine Kinase | 0.25 mg/mL |
| DsbC | 0.4 mg/mL |
| 17 RNA polymerase | 66.6 µg/mL |
| E. coli S30 extract-DTT (A260 of S30 extract = 228) | 30 vol % |
| Template DNA (expression vector) | 1 µg/mL each |

TABLE 6

| Composition of dialysis external solution | Concentration |
| --- | --- |
| LMCP(D-Glu)-tRNA-DTT | 37.3 vol % |
| Sodium azide | 0.05 vol % |
| Magnesium acetate | 6 to 8 mM |
| Amino acid-DTT (20 types) | 1.0 mM each |
| Reduced glutathione | 2.5 mM |
| Oxidized glutathione | 2.5 mM |
| IPTG | 0.5 mM |
| S30 buffer-OTT | 30 vol % |

After the reaction, the total fraction (T) and the soluble fraction (S) of the reaction solution were subjected to 15% Tricine-SDS-PAGE and then stained with CBB. The results are shown in FIG. 13 and FIG. 14.

Figure 13:
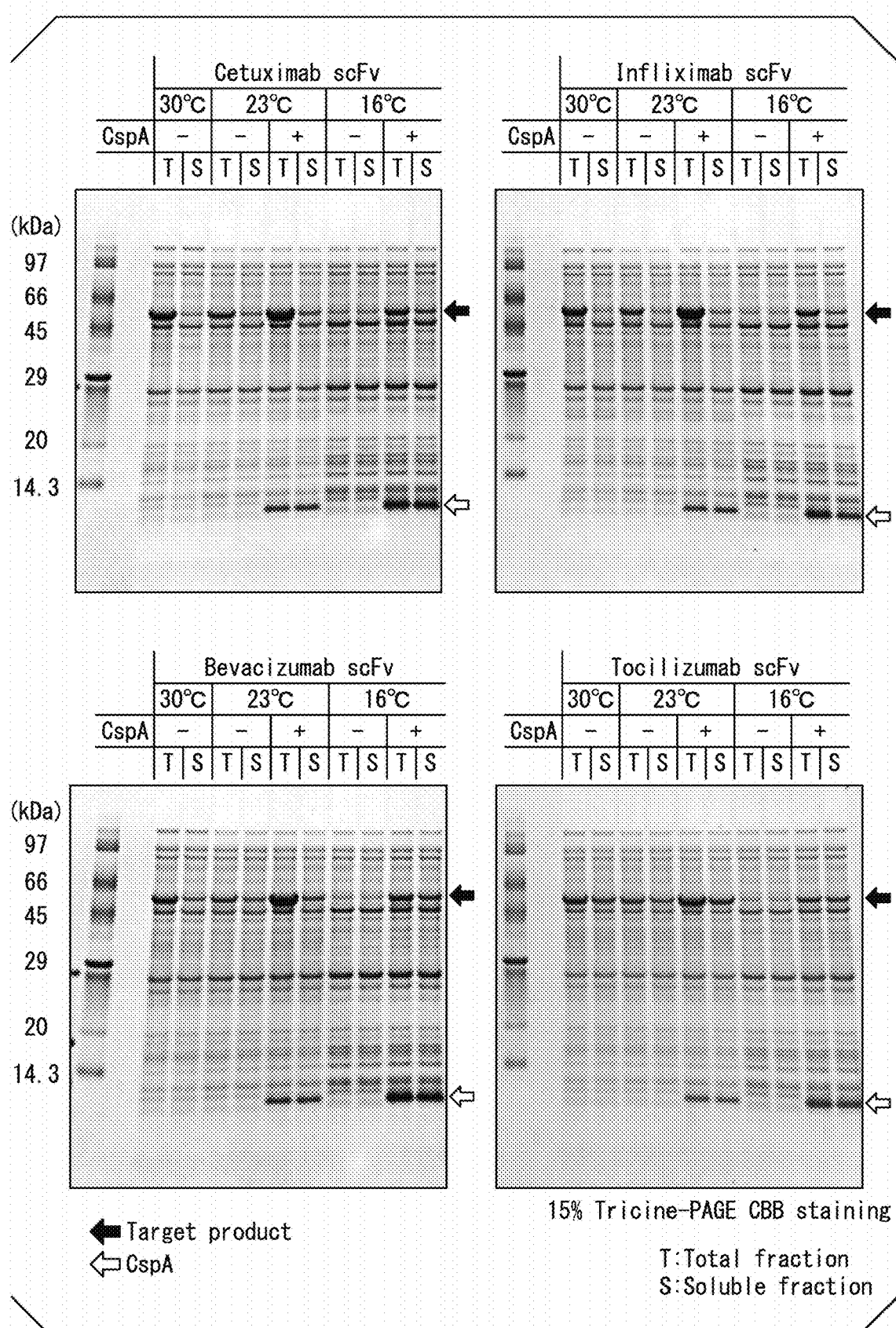
FIG. 13 shows the electrophoresis results with respect to the total fraction (T) and the soluble fraction (S) after the synthesis reaction of each small molecule antibody (single chain antibody) in Example 10.
Figure 14:
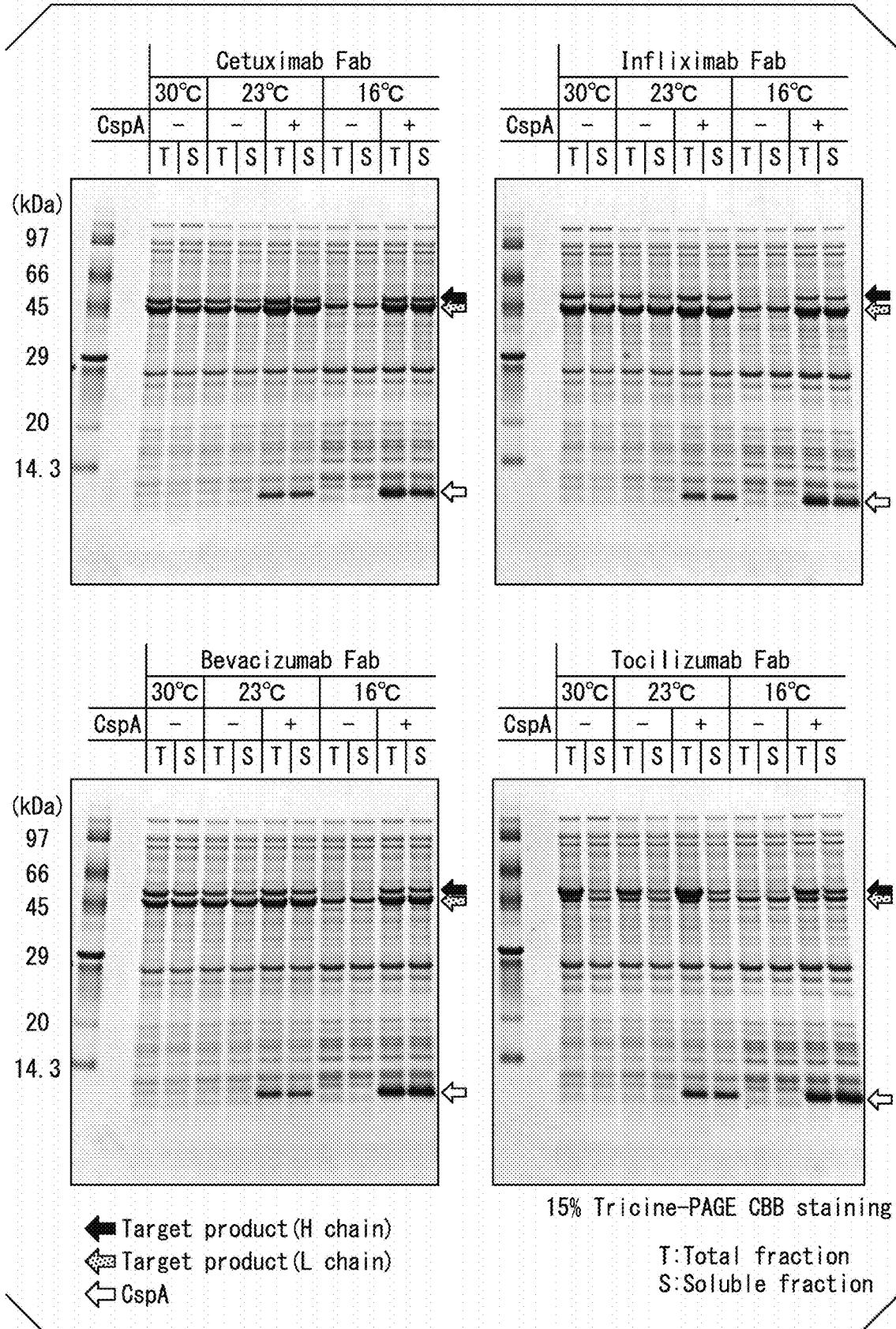
FIG. 14 shows the electrophoresis results with respect to the total fraction (T) and the soluble fraction (S) after the synthesis reaction of each small molecule antibody (Fab) in Example 10.

As shown in FIG. 13 and FIG. 14, even in the case of H chains of scFv and Fab, which are highly prone to precipitation when synthesized at a reaction temperature of 30° C. or 23° C., the precipitation was suppressed with the reaction temperature of 16° C. In addition, the reaction implemented in the presence of CspA showed an increase in the protein yield while maintaining high solubility.

Example 11 Protein Synthesis in the Presence of Multiple Types of Csps

Following the same procedure as in Example 6, GFPS1 was synthesized with a reaction time of 6 hours and a reaction temperature of 16° C. in the presence of CspA, CspB, CspC, CspD, CspE, CspG, CspH and CspI, each derived from *Escherichia coli*, SliCspC derived from *Shewanella livingstonensis*, and BsuCspB derived from *Bacillus subtilis*.

Figure 15:
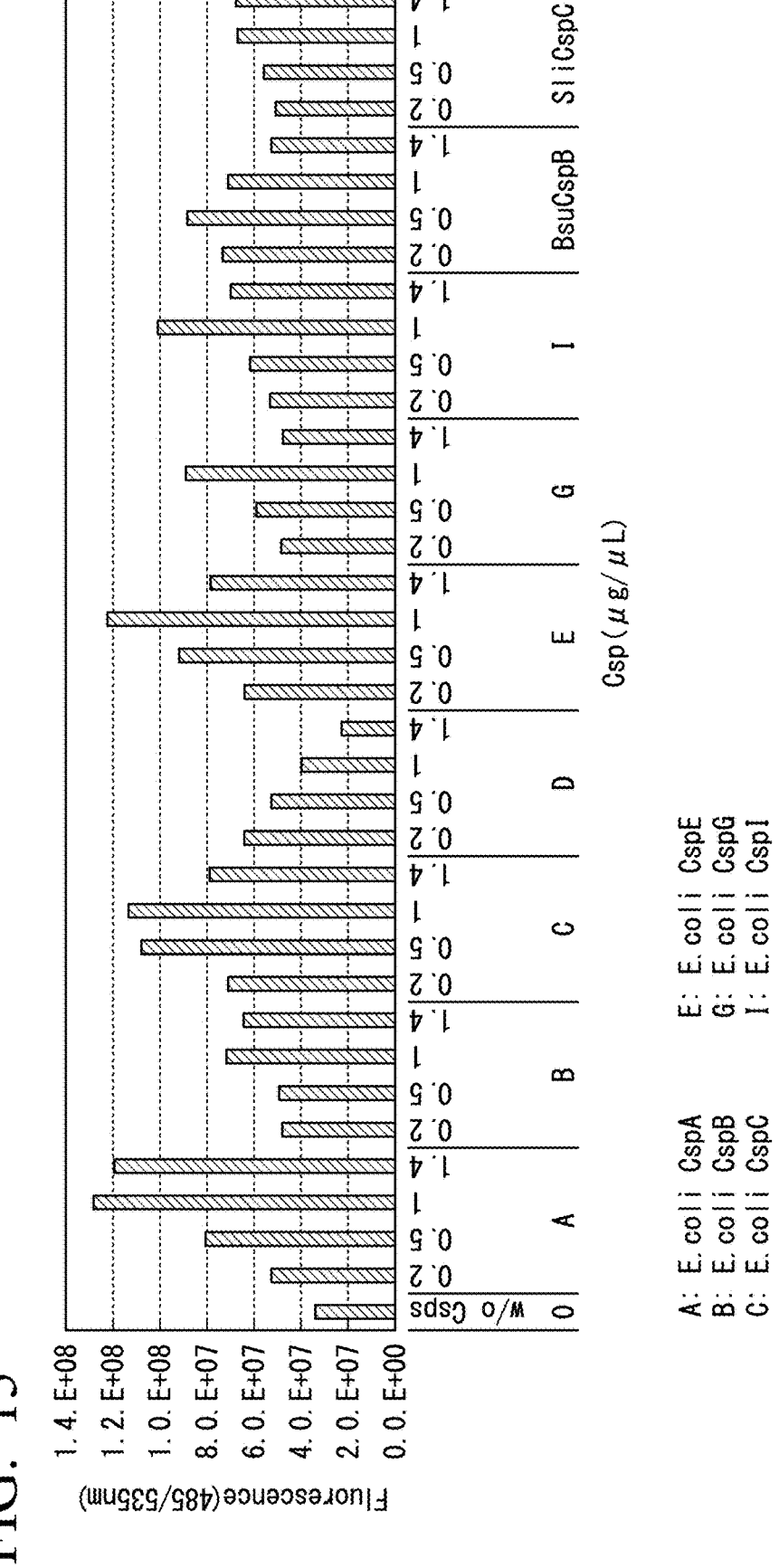
FIG. 15 is a diagram showing the Csp concentration dependence of the yield of GFPS1 synthesized in Example 11.
Figure 16:
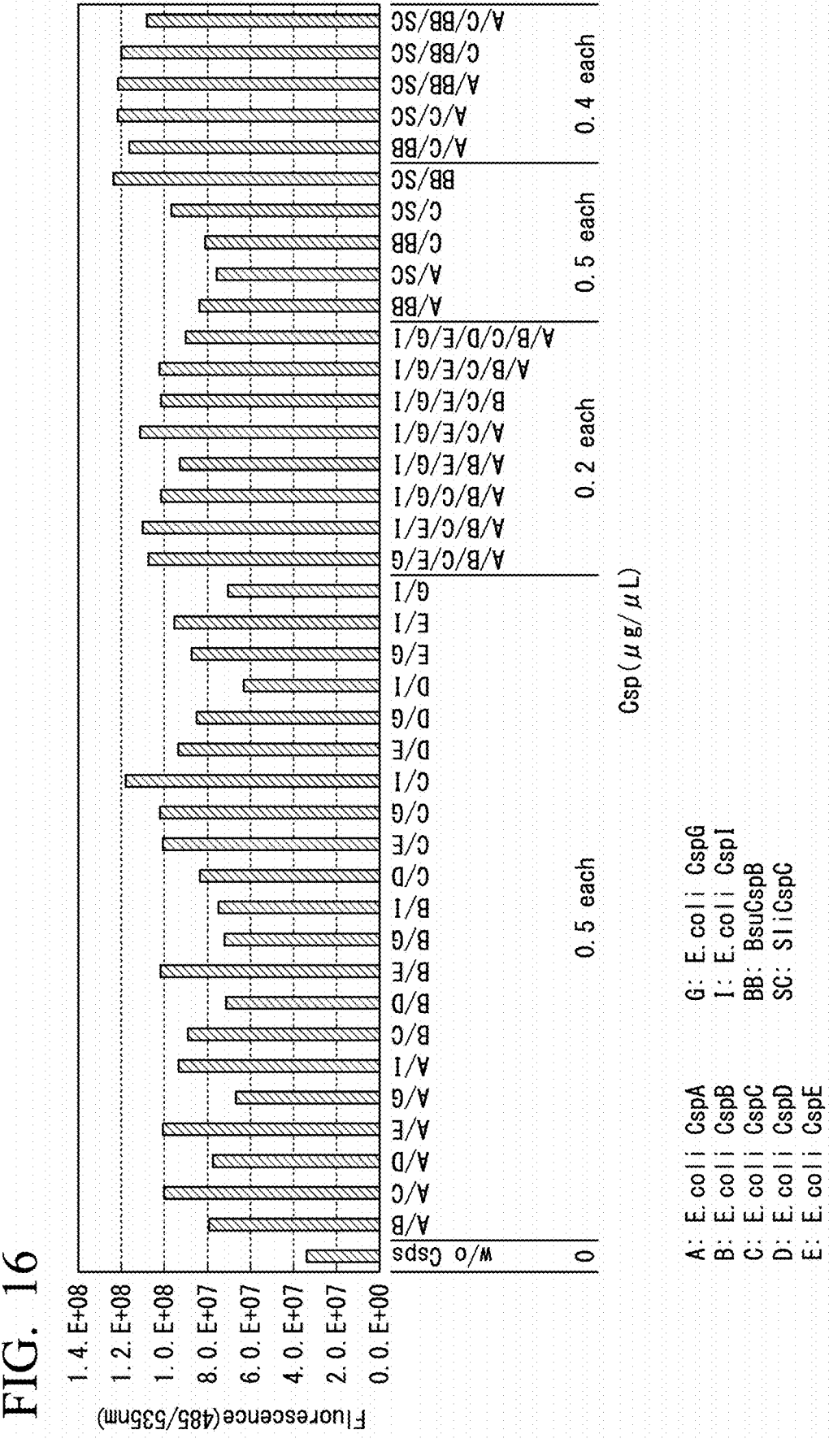
FIG. 16 is a diagram showing the Csp complementarity of the yield of GFPS1 synthesized in Example 11.

The fluorescence intensity of GFPS1 was measured in the same manner as in Example 1. The Csp concentration dependence of the yield of GFPS1 (CSP addition amounts: 0.2, 0.5, 1.0, 1.4 µg/µL) is shown in FIG. 15, and the Csp complementarity of the yield of GFPS1 is shown in FIG. 16. The expression "A/B, 0.5 each" in FIG. 16 means that each of the amounts of CspA and CspB added was 0.5 µg/µL, and other like notations have like meanings.

As shown in FIG. 15, CspA, CspB, CspC, CspE, CspG and CspI, each derived from *Escherichia coli*, SliCspC derived from *Shewanella livingstonensis*, and BsuCspB derived from *Bacillus subtilis* increased the yield of GFPS1 synthesized in the batch method as well. In addition, as shown in FIG. 16, multiple species of Csp that increase the yield showed complementary effect.

The invention claimed is:

1. A protein production method comprising producing a protein with a reaction solution of a cell-free protein synthesis system containing either one or both of a cold shock protein and a nucleic acid containing a coding region encoding an amino acid sequence of the cold shock protein, wherein the method is implemented at a reaction temperature of 4 to 23° C., and wherein the reaction solution contains the cold shock protein in an amount of 0.5 to 1.5 µg/µL, wherein the amount of the produced protein is greater than that obtained under conditions in which at least one of the reaction temperature and the amount of the cold shock protein falls outside the respective range.

2. The protein production method according to claim 1, wherein the cold shock protein is cold shock protein A (CspA), cold shock protein B (CspB), cold shock protein C (CspC), cold shock protein E (CspE), cold shock protein G (CspG), or cold shock protein I (CspI) derived from *Escherichia coli*.

3. The protein production method according to claim 2, wherein the cold shock protein is the CspA and derived from *Escherichia coli*.

4. The protein production method according to claim 1, wherein the cold shock protein is an S-layer cold shock protein C (SliCspC) derived from *Shewanella livingstonensis* of the genus *Shewanella*.

5. The protein production method according to claim 1, wherein the cold shock protein is BsuCspB derived from *Bacillus subtilis* of the genus *Bacillus*.

6. The protein production method according to any one of claim 1, wherein the reaction solution is a solution containing a cell extract.

7. The protein production method according to claim 6, wherein the cell extract is a cell extract derived from *Escherichia coli*.

8. The protein production method according to claim 7, wherein the reaction solution contains an L-amino acid, a buffer solution, a salt, an energy source, and an energy regeneration system.

9. A cell-free protein synthesis kit comprising one or both of the cold shock protein and the nucleic acid, and the reaction solution according to claim 1.

* * * * *